(12) United States Patent
Takizawa et al.

(10) Patent No.: US 10,532,227 B2
(45) Date of Patent: Jan. 14, 2020

(54) PARTICLE BEAM TREATMENT SYSTEM

(71) Applicant: Hitachi, Ltd., Tokyo (JP)

(72) Inventors: Kenichi Takizawa, Tokyo (JP); Tomoki Murata, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 410 days.

(21) Appl. No.: 15/448,685

(22) Filed: Mar. 3, 2017

(65) Prior Publication Data
US 2017/0252581 A1 Sep. 7, 2017

(30) Foreign Application Priority Data
Mar. 4, 2016 (JP) .................... 2016-042740

(51) Int. Cl.
*A61N 5/10* (2006.01)
(52) U.S. Cl.
CPC ......... *A61N 5/1077* (2013.01); *A61N 5/1048* (2013.01)
(58) Field of Classification Search
CPC .. A61N 5/10–1087; H05H 7/00–15/00; H05H 2277/00–1405
See application file for complete search history.

(56) References Cited

U.S. PATENT DOCUMENTS

| | | | | |
|---|---|---|---|---|
| 5,349,198 | A | * | 9/1994 | Takanaka ................ A61N 5/10 250/396 ML |
| 2002/0030164 | A1 | * | 3/2002 | Akiyama ................ A61N 5/10 250/492.1 |
| 2005/0161618 | A1 | * | 7/2005 | Pedroni ................... A61N 5/10 250/492.3 |
| 2008/0067451 | A1 | * | 3/2008 | Guertin ................... A61N 5/10 250/503.1 |
| 2010/0111264 | A1 | * | 5/2010 | Henderson ............ A61N 5/10 378/197 |

FOREIGN PATENT DOCUMENTS

| | | | | |
|---|---|---|---|---|
| EP | 1075855 | A1 | * 2/2001 | ............. A61N 5/01 |
| JP | 2002-113118 | A | 4/2002 | |
| JP | 2004-121309 | A | 4/2004 | |

* cited by examiner

*Primary Examiner* — Catherine B Kuhlman
(74) *Attorney, Agent, or Firm* — Mattingly & Malur, PC

(57) ABSTRACT

There is provided a particle beam treatment system which has a simple mechanism and which is excellent in maintainability. Irradiation devices 10a and 10b respectively have a plurality of irradiation ports 102a, 102b, and 102c for irradiating a target with a particle beam in a plurality of directions. In addition, an irradiation nozzle unit 105 of the irradiation devices 10a and 10b is movable between the plurality of irradiation ports 102a, 102b, and 102c. A fixed cover structure 107 is disposed between the plurality of irradiation ports 102a, 102b, and 102c and the irradiation nozzle unit 105. In addition, the cover structure 107 has a slit 110 for allowing the irradiation nozzle unit 105 to move therethrough.

10 Claims, 8 Drawing Sheets

[Fig. 1]
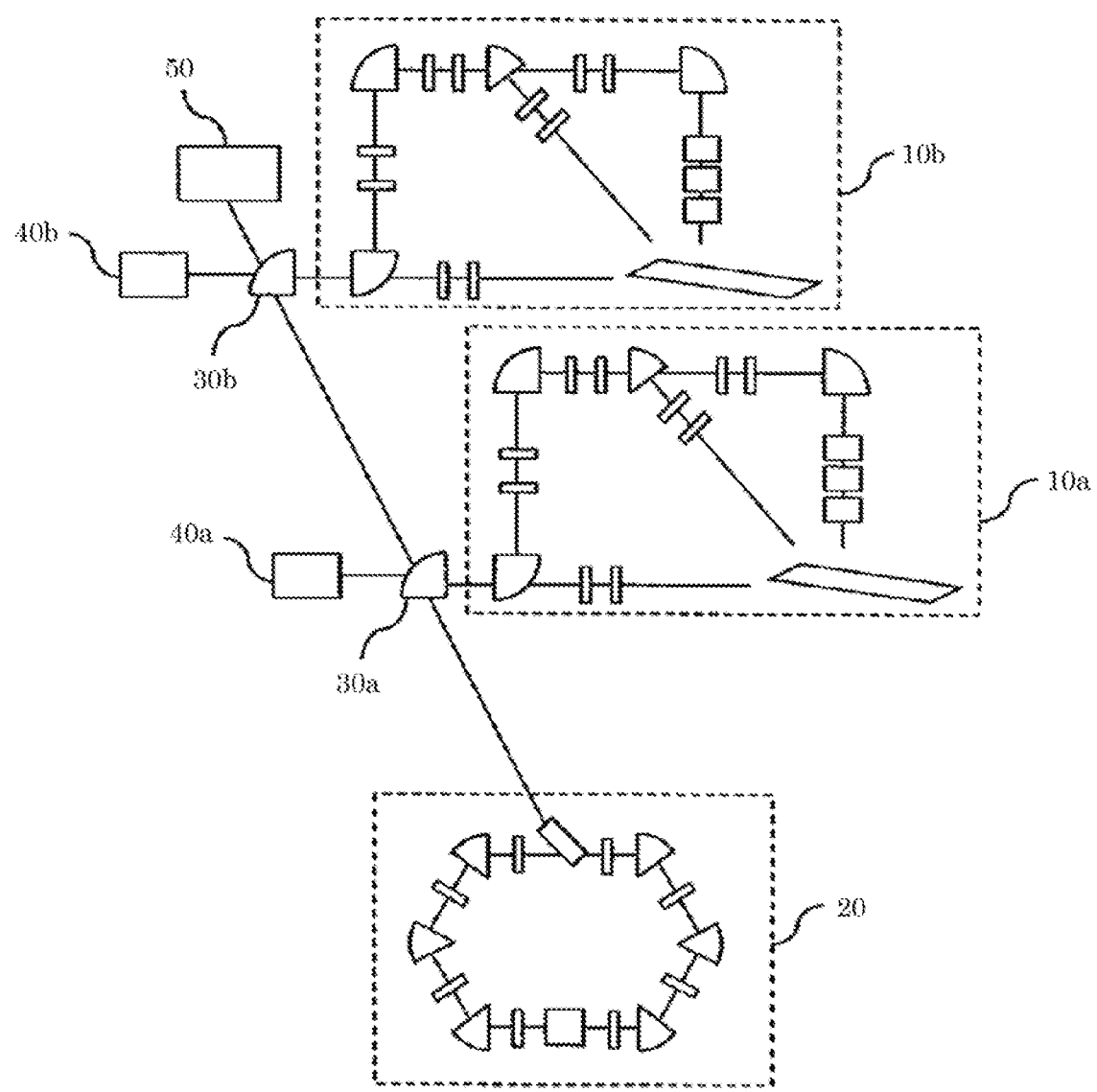

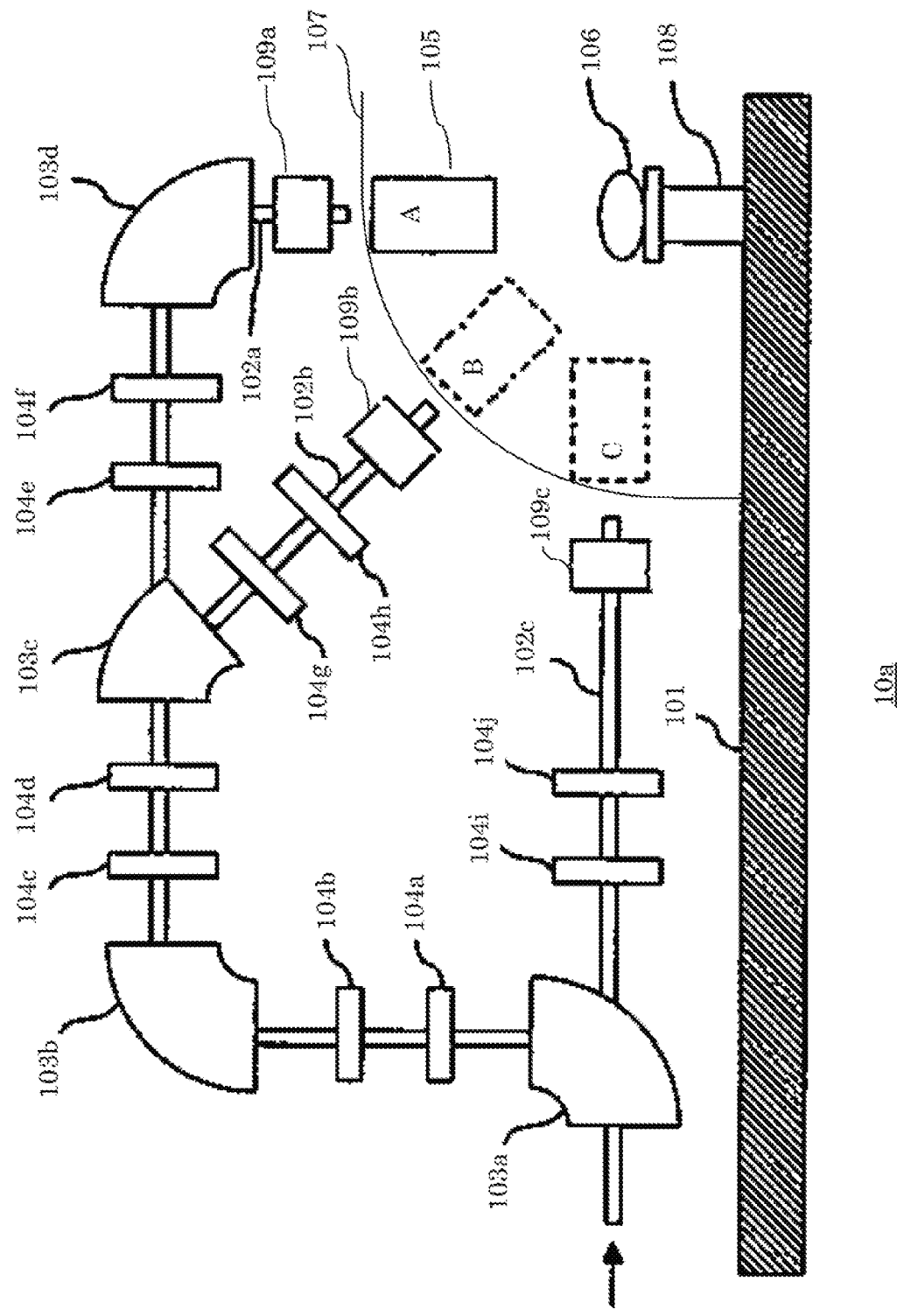
[Fig. 2]

[Fig. 3]
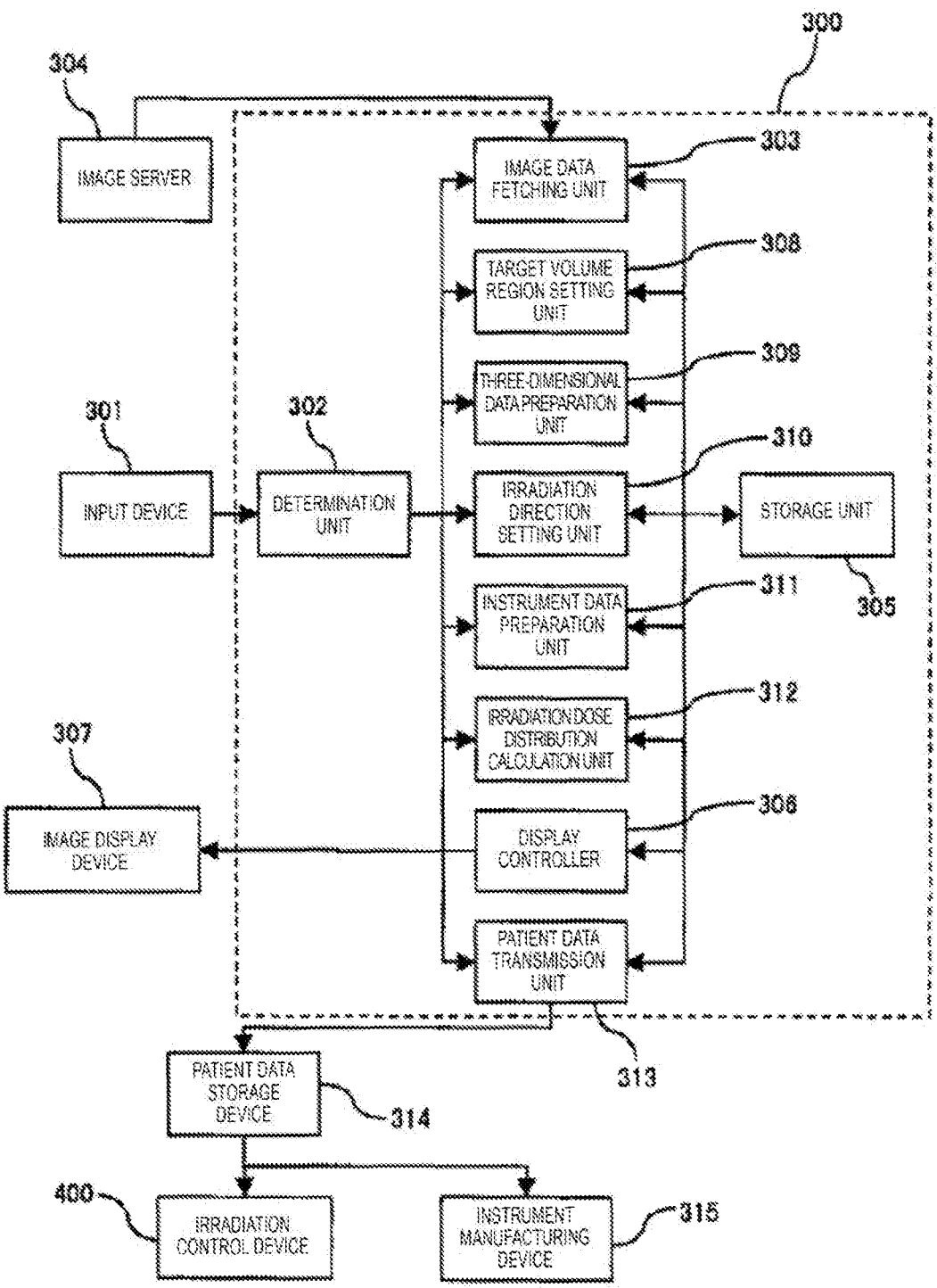

[Fig. 4]
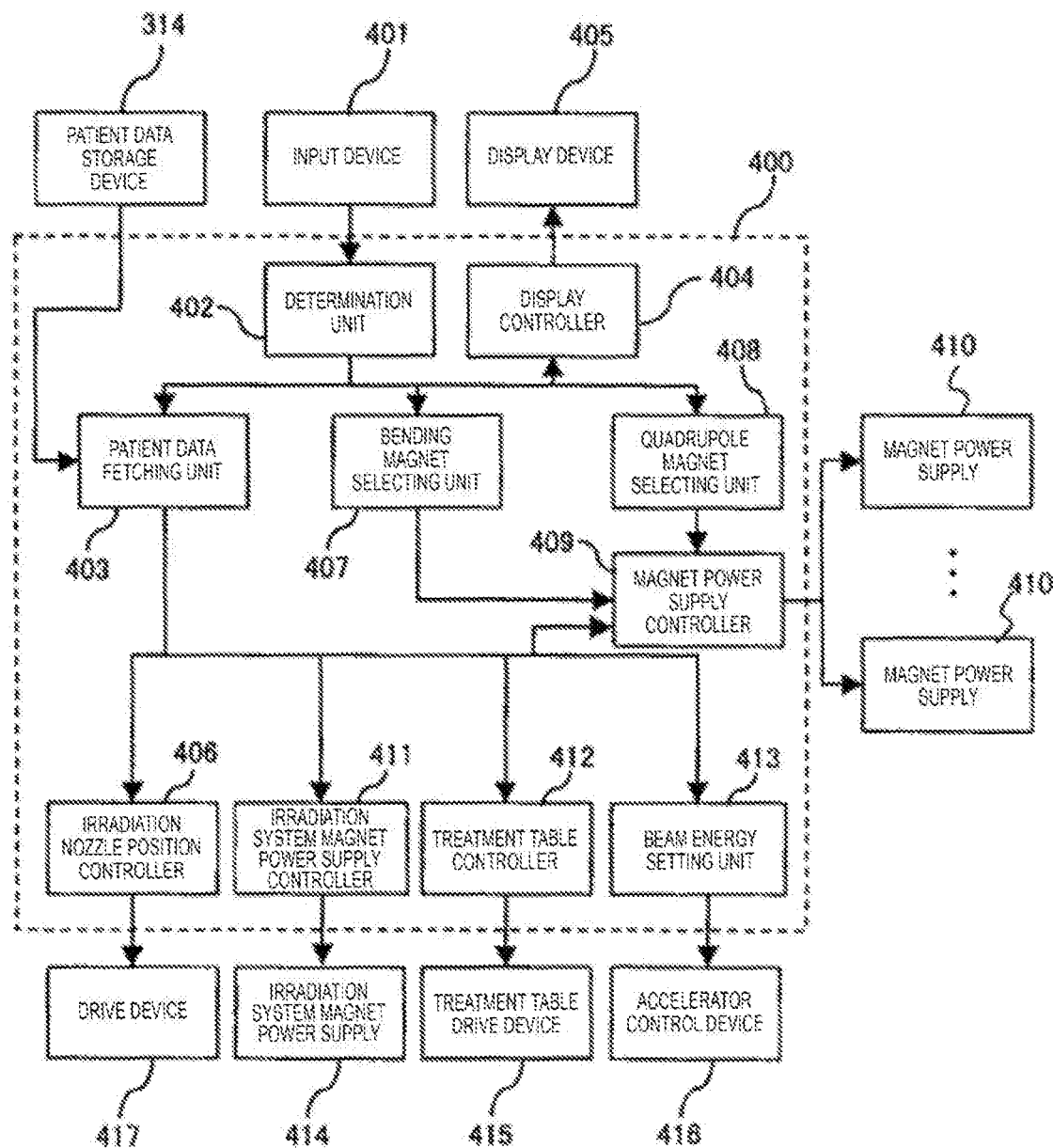

[Fig. 5]
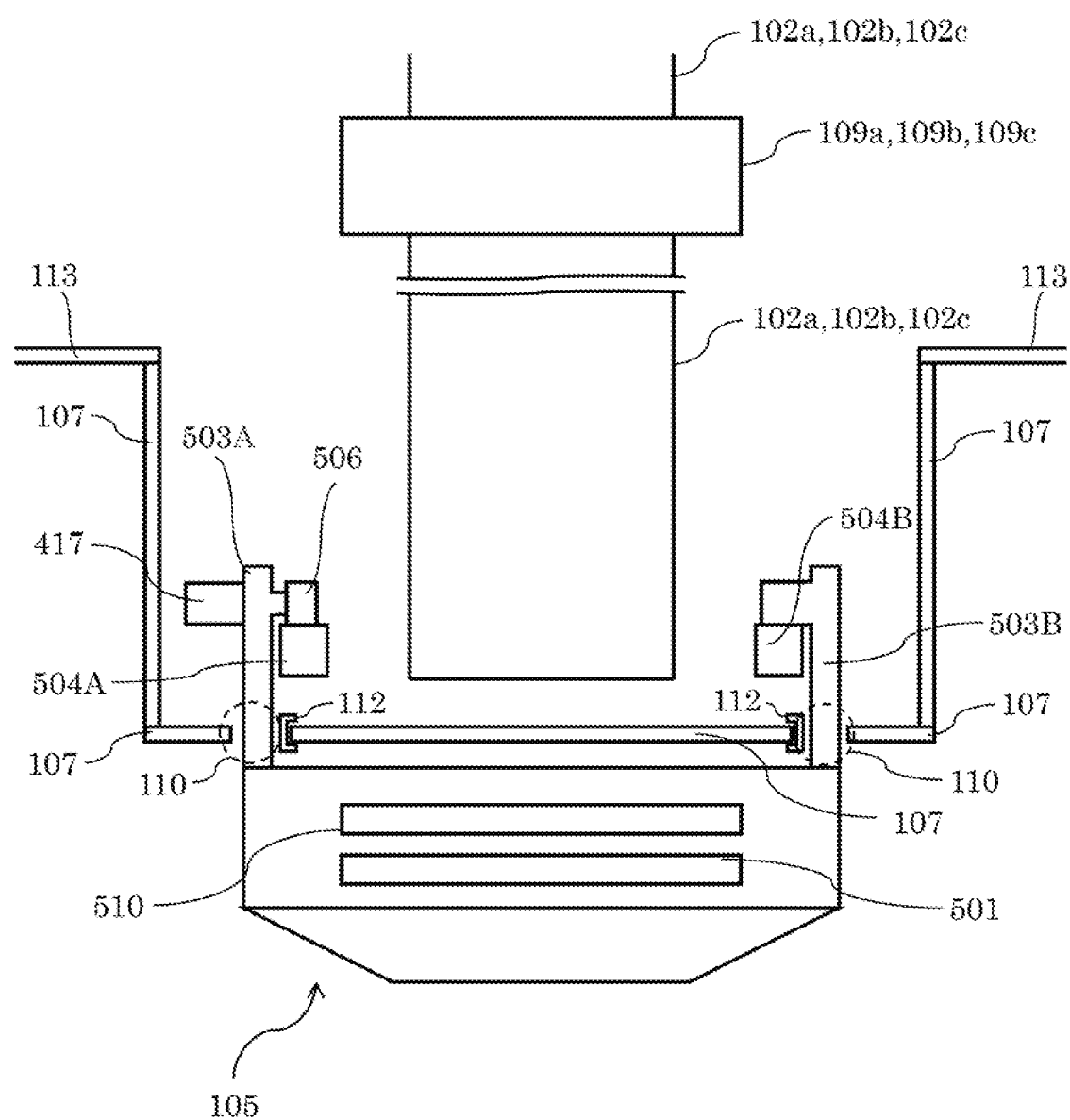

[Fig. 6]
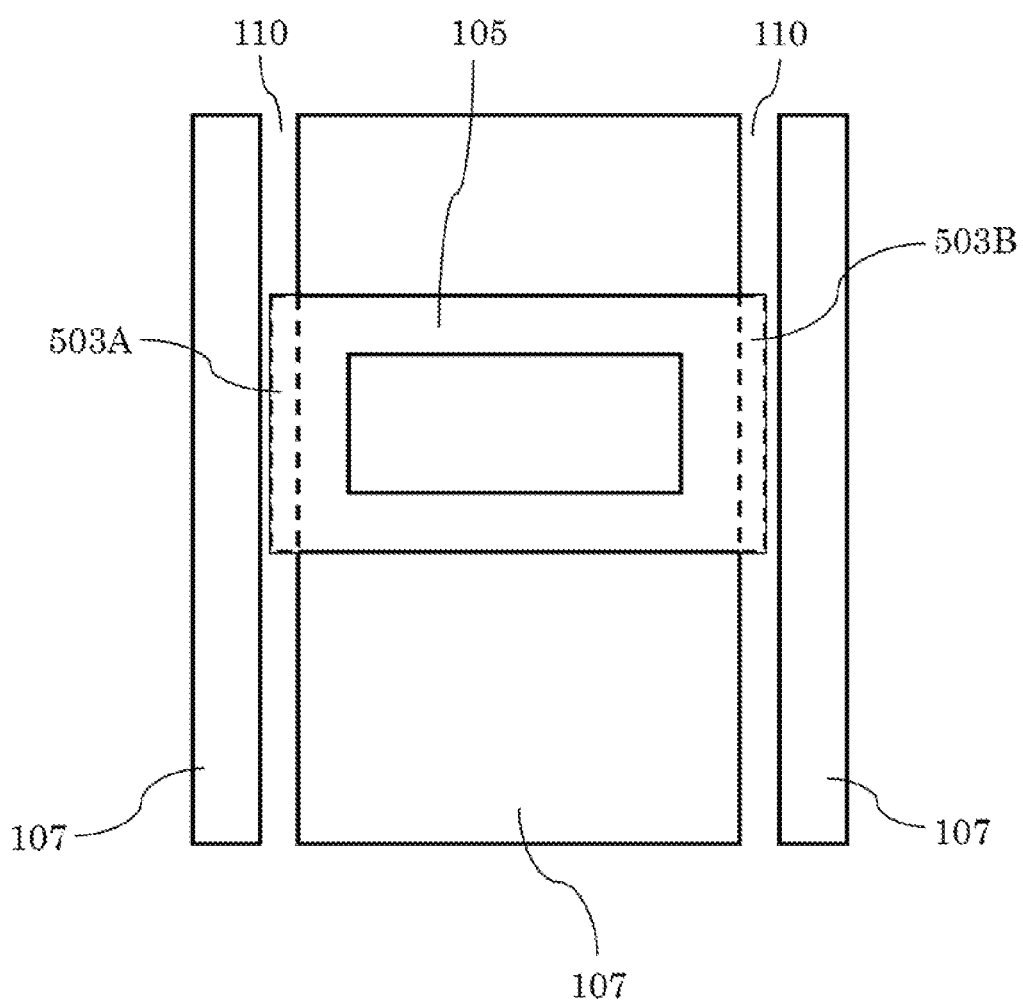

[Fig. 7]
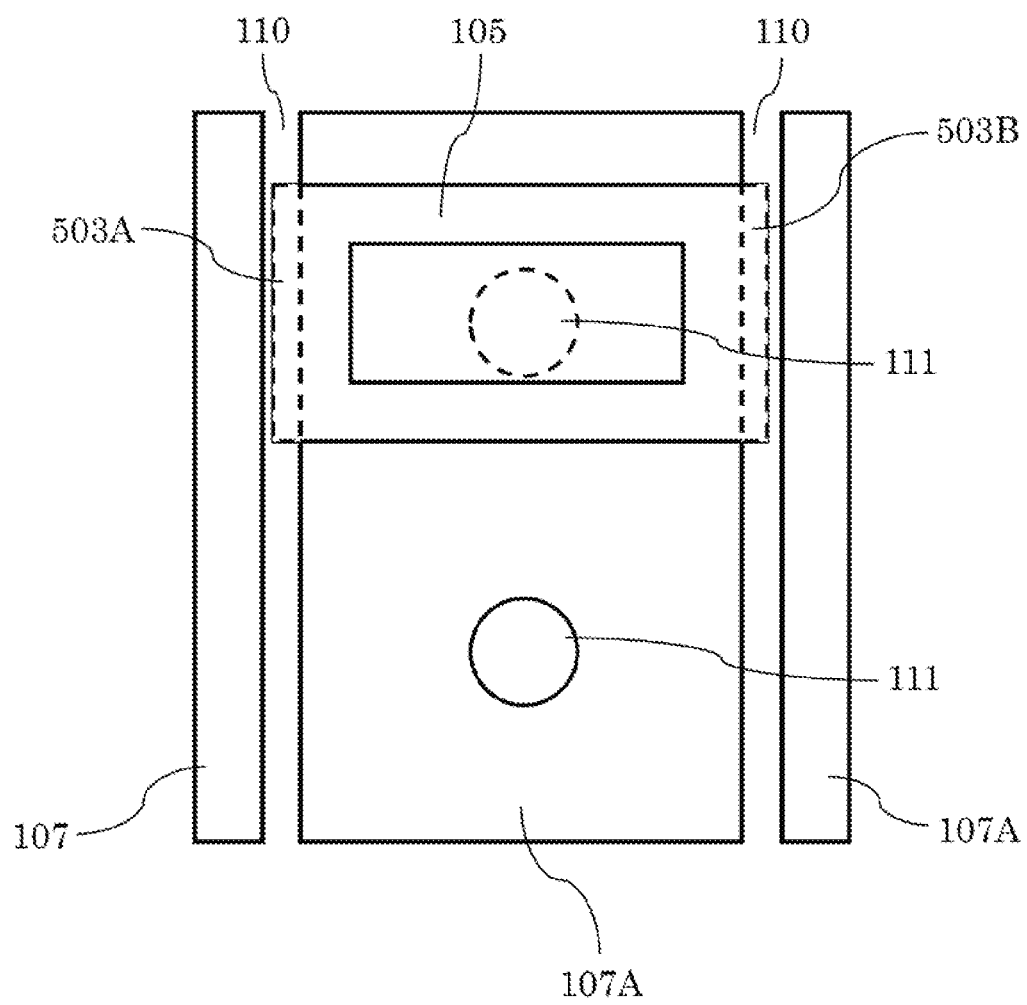

[Fig. 8]
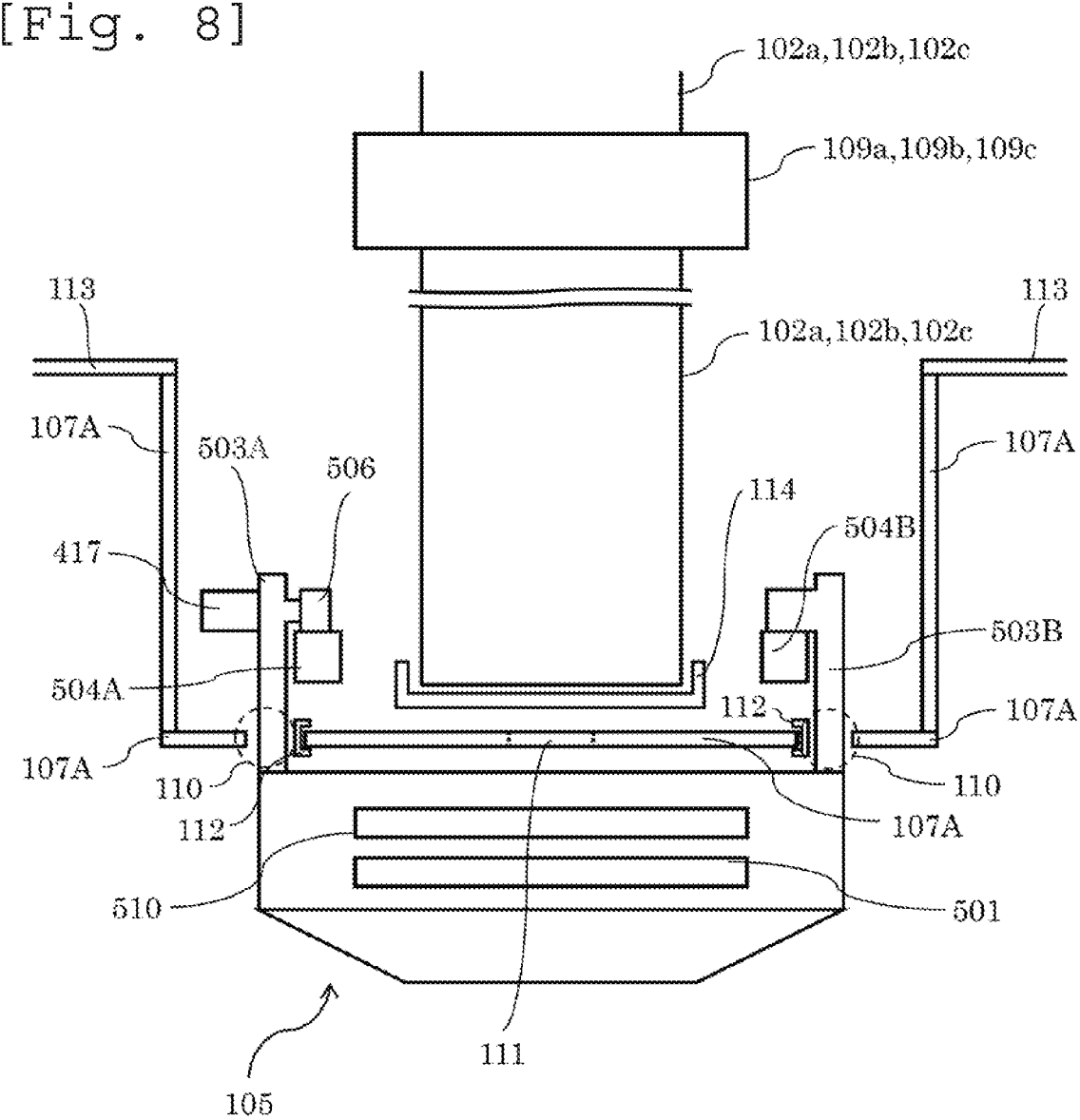

PARTICLE BEAM TREATMENT SYSTEM

TECHNICAL FIELD

The present invention relates to a particle beam treatment system.

BACKGROUND ART

PTL 1 discloses a technique which can further simplify a structure, and which aims to form a substantially horizontal access floor even if an irradiation unit for extracting a particle beam is located at any position. The technique includes a rotating gantry in which a particle beam irradiation unit for extracting the particle beam is installed, an annular frame that is supported inside the rotating gantry so as to be relatively rotatable, a fixed annular frame that is disposed to face the annular frame, a co-rotation preventing mechanism that comes into contact with both the annular frames so as to prevent co-rotation of the annular frame rotated due to the rotation of the rotating gantry, and a bendable moving floor that is disposed between the annular frames, that movably engages with the annular frames so as to cause a lower side to be substantially horizontal, and that further moves due to the rotation of the rotating gantry.

In addition, PTL 2 discloses the following technique. In a case where an irradiation target is irradiated with beams in a plurality of directions, in order to reduce the cost, an irradiation nozzle unit configured to include a wobbler magnet, a scatterer, a range modulator, a patient collimator, and a patient bolus is shared in use with a plurality of irradiation ports for outputting a charged particle beam to the irradiation target in the plurality of directions.

CITATION LIST

Patent Literature

PTL 1: JP-A-2004-121309
PTL 2: JP-A-2002-113118

SUMMARY OF INVENTION

Technical Problem

In recent years, in cancer treatment using radiation, attention has been paid to a particle beam (proton beam or heavy particle beam) which can be used in the treatment without causing damage to normal cells comparatively.

In order to efficiently perform particle beam irradiation, it is necessary to accurately irradiate a target volume of a patient with the particle beam. Accordingly, a radiation treatment device has been developed which has a structure capable of setting an irradiation nozzle so as to be located at an optimal irradiation position for the patient.

In the irradiation nozzle which irradiates the irradiation target with the particle beam, a vacuum duct through which the particle beam passes, an instrument for adjusting distribution of a dose to be administered are installed along a particle beam path. Consequently, it is difficult to form a compact structure.

As disclosed in PTL 1 or PTL 2, in a case where the irradiation nozzle is movable in a circumferential direction while a distal end thereof is oriented to the irradiation target, a structure (moving floor) which is deformable along the movement of the irradiation nozzle is installed in order to form an access floor or so as to function as a cover for concealing a drive structure for moving the irradiation nozzle. However, in a case of employing the deformable moving floor, there is a problem in that a mechanism becomes complicated. In addition, due to the complicated mechanism, there is also a problem in that it takes time to carry out maintenance work.

Therefore, the present invention aims to provide a particle beam treatment system which has a simple mechanism and which is excellent in maintainability.

Solution to Problem

For example, in order to solve the above-described problems, the present invention adopts configurations disclosed in claims.

The present invention includes a plurality of means for solving the above-described problems. As an example thereof, there is provided a particle beam treatment system including an accelerator that accelerates a particle beam, a beam transport system that transports the particle beam accelerated by the accelerator, an irradiation device that has an irradiation nozzle for irradiating a target with the particle beam transported by the beam transport system, and a control device that controls the accelerator, the beam transport system, and the irradiation device. The irradiation device has a plurality of irradiation ports for irradiating the target with the particle beams in a plurality of directions. The irradiation nozzle of the irradiation device is movable between the plurality of irradiation ports. A fixed cover member is disposed between the plurality of irradiation ports and the irradiation nozzle.

Advantageous Effects of Invention

According to the present invention, it is possible to provide a particle beam treatment system which has a simple mechanism and which is excellent in maintainability.

BRIEF DESCRIPTION OF DRAWINGS

FIG. 1 is a configuration diagram of a particle beam treatment system which is a preferred embodiment according to the present invention.

FIG. 2 is a configuration diagram of a particle beam irradiation device in the particle beam treatment system in FIG. 1.

FIG. 3 is a configuration diagram of a treatment planning system which prepares a treatment plan for the particle beam treatment system in FIG. 1.

FIG. 4 is a configuration diagram of an irradiation control device which controls the particle beam irradiation device in FIG. 2.

FIG. 5 is a view illustrating a schematic configuration when an irradiation nozzle and a cover member according to Embodiment 1 are viewed in a direction parallel to beam irradiation.

FIG. 6 is a view illustrating a schematic configuration when the irradiation nozzle and the cover member according to Embodiment 1 are viewed from a treatment table side.

FIG. 7 is a view illustrating a schematic configuration when an irradiation nozzle and a cover member according to Embodiment 2 are viewed from a treatment table side.

FIG. 8 is a view illustrating a schematic configuration when an irradiation nozzle and a cover member according to Embodiment 3 are viewed in the direction parallel to the beam irradiation.

DESCRIPTION OF EMBODIMENTS

Hereinafter, embodiments of a particle beam treatment system according to the present invention will be described with reference to the drawings.

<Embodiment 1>

Embodiment 1 of the particle beam treatment system according to the present invention will be described with reference to FIGS. 1 to 6. In the present embodiment, a particle beam treatment system which irradiates a target with a heavy particle such as a carbon ion will be described as an example of the particle beam treatment system.

First, a treatment system illustrated in FIG. 1 will be described. FIG. 1 is a view illustrating a configuration of the particle beam treatment system which is a preferred embodiment according to the present invention.

In FIG. 1, the particle beam treatment system includes a synchrotron 20 that accelerates a heavy particle beam (hereinafter, referred to as a beam), a beam transport system that transports the beam accelerated by the synchrotron 20, irradiation devices 10a and 10b that has an irradiation nozzle unit (irradiation nozzle) 105 (refer to FIG. 2) for irradiating a target with the beam transported by the beam transport system, and an irradiation control device 400 (refer to FIG. 4) that controls an operation of each instrument inside the synchrotron 20, the beam transport system, and the irradiation devices 10a and 10b.

In the synchrotron 20, after the beam is accelerated, the beam is extracted to the beam transport system. The extracted beam is guided to a switching magnet 30a. When excited, the switching magnet 30a deflects the beam, and guides the beam to the irradiation device 10a. When not excited, the switching magnet 30a does not deflect the beam, and causes the beam to move straight forward. The switching magnet 30a is excited by power supplied from a power supply 40a. The power supply from the power supply 40a is controlled by an operator operating a switch of a control panel (not illustrated). That is, when a patient 106 is treated in the irradiation device 10a, the operator operates the switch so as to supply the power from the power supply 40a to the switching magnet 30a. When the patient 106 is not treated in the irradiation device 10a, the operator operates the switch so as to stop power supply from the power supply 40a to the switching magnet 30a. In the irradiation control device 400, switching may be automatically performed. In the irradiation device 10a, a target volume of the patient 106 is irradiated with the guided beam. Details will be described later.

In a case where the treatment is performed using the irradiation device 10b, the power supply to the switching magnet 30a is stopped, and the power is supplied to the switching magnet 30b. Similarly to a case of the above-described switching magnet 30a, the power is supplied to the switching magnet 30b by the operator operating the switch so as to control a power supply 40b. The power supply to the switching magnet 30a, and the power is supplied to the switching magnet 30b. In this manner, after the beam moves straight forward in the switching magnet 30a in a state where the switching magnet 30a is not excited, the beam is deflected by the switching magnet 30b in a state of being excited, and is guided to the irradiation device 10b. The treatment in the irradiation device 10b is substantially the same as irradiation in the irradiation device 10a to be described later, and description thereof will be omitted.

In a case where the treatment is not performed using the irradiation devices 10a and 10b, beam extraction from the synchrotron 20 is stopped, or both the switching magnets 30a and 30b are brought into a non-excited state so as to dump the beam into a beam dump 50.

Next, beam irradiation in the irradiation device 10a will be described in detail with reference to FIG. 2. FIG. 2 is a view illustrating a configuration of the particle beam irradiation device belonging to the particle beam treatment system in FIG. 1.

The irradiation device 10a according to the present embodiment illustrated in FIG. 2 is configured to be capable of irradiating the patient 106 with the beam in three directions. That is, the irradiation device 10a has a vacuum duct 102a disposed to be vertical to a floor 101, a vacuum duct 102b disposed to be tilted by 45° from the floor 101, and a vacuum duct 102c disposed to be horizontal to the floor 101. In the irradiation device 10a, a beam irradiation direction is changed by changing the vacuum duct for guiding the beam. In the present embodiment, the vacuum ducts 102a to 102c are respectively called irradiation ports 102a to 102c.

In a case where the beam irradiation is performed in a direction vertical to the floor 101, bending magnets 103a, 103b, and 103d are excited, and quadrupole magnets 104a to 104f are excited. In addition, at this time, the bending magnet 103c is brought into a non-excited state. As described above, the beam extracted from the synchrotron 20 is guided to the bending magnet 103a of the irradiation device 10a, and is deflected by the bending magnets 103a, 103b, and 103d. The beam is subjected to tune adjustment by the quadrupole magnets 104a to 104f, and is guided to the irradiation port 102a.

After the beam is output from the irradiation port 102a, and the beam passes through the irradiation nozzle so as to be used in irradiating the patient 106 on a treatment table 108. Here, the irradiation nozzle in the irradiation device 10a according to the present embodiment includes an irradiation nozzle unit 105 which is movable between the plurality of irradiation ports 102a, 102b, and 102c. Therefore, the irradiation nozzle unit 105 is moved in advance to a position (position A in FIG. 2) through which the beam output from the irradiation port 102a passes. A limit switch is disposed at the position through which the beam output from the irradiation port 102a passes. The irradiation nozzle unit 105 is moved to the position of the limit switch by controlling a drive device (not illustrated) disposed in the irradiation nozzle unit 105. In this way, according to the present embodiment, the limit switch and the drive device are used as a moving mechanism for moving the irradiation nozzle. According to the above-described configuration, the patient 106 is irradiated with the beam via the irradiation port 102a. In this manner, the patient 106 can be irradiated with the beam in the direction vertical to the floor 101.

Next, a case will be described where the patient 106 is irradiated with the beam in the direction tilted by 45° from the floor 101. First, the irradiation nozzle unit 105 is moved to a position (position B in FIG. 2) through which the beam output from the irradiation port 102b passes. Thereafter, the bending magnets 103a to 103c, and the quadrupole magnets 104a to 104d, 104g, and 104h are brought into an excited state. The beam guided to the bending magnet 103a is guided to the irradiation port 102b by the bending magnets 103a to 103c, and the quadrupole magnets 104a to 104d, 104g, and 104h. The patient 106 is irradiated with the guided beam via the irradiation port 102b and the irradiation nozzle unit 105. In this way, the patient 106 is irradiated with the beam via the irradiation port 102b, thereby enabling the patient 106 to be irradiated with the beam in the direction tilted by 45° from the floor 101.

Furthermore, a case will be described where the patient 106 is irradiated with the beam in the direction horizontal to the floor 101. First, the irradiation nozzle unit 105 is moved to a position (position C in FIG. 2) through which the beam output from the irradiation port 102c passes. Thereafter, the quadrupole magnets 104i and 104j are brought into an excited state. At this time, the bending magnet 103a is always brought into a non-excited state. The beam guided to the bending magnet 103a moves straight forward without being deflected by the bending magnet 103a. The beam is subjected to tune adjustment by the quadrupole magnets 104i and 104j, and thereafter, is guided to the irradiation port 102c. The patient 106 is irradiated with the beam via the irradiation port 102c and the irradiation nozzle unit 105. In this manner, the patient 106 is irradiated with the beam via the irradiation port 102c, thereby enabling the patient 106 to be irradiated with the beam in the direction horizontal to the floor 101.

As described above, the irradiation device 10a according to the present embodiment can irradiate the patient 106 with the beam in three directions. The irradiation device 10a can irradiate the patient 106 with the beam in three directions by disposing three irradiation ports. In addition, a couch which can be tilted is employed as the treatment table 108. Accordingly, a beam irradiation direction for the target volume can be adjusted by changing an orientation of the patient 106.

Furthermore, as illustrated in FIG. 2, a cover structure (cover member) 107 us disposed so as to separate a space having the irradiation nozzle unit 105 installed therein and a space having the plurality of irradiation port 102a, 102b, and 102c installed therein from each other. The cover structure 107 configures a wall surface of a place through which the irradiation nozzle unit 105 moves and passes. That is, the moving mechanism for moving the irradiation nozzle unit 105 is installed so as to be concealed from the view of the patient and so as to be partially visible through a side wall 113 of a treatment room. The cover structure 107 is fixed to the floor 101.

The cover structure 107 has a structure which does not need to be intentionally deformed in order to evacuate the cover structure 107 from a passage of the irradiation nozzle unit 105 due to the movement of the irradiation nozzle unit 105. The irradiation nozzle unit 105 is structurally separated from the respective irradiation ports 102a to 102c. The cover structure 107 configures the irradiation nozzle unit 105 located ahead so as to maintain irradiation accuracy even when the vacuum duct is intermediately disconnected thereto. In addition, a sufficient space through which the fixed cover structure 107 can pass is secured in the beam passing path. In addition, the irradiation nozzle unit 105 is attached to the moving mechanism so that a side on which the treatment table 108 of the cover structure 107 is installed can be moved along the cover structure 107. A specific structure of the cover structure 107 and a configuration of the moving mechanism of the irradiation nozzle unit 105 will be described later.

Next, a specific control method of the irradiation device 10a will be described herein with reference to FIGS. 3 and 4. Many instruments configuring the irradiation device 10a is controlled based on a predetermined treatment plan. Thus, a preparing method of the treatment plan will be described with reference to FIG. 3. FIG. 3 is a view illustrating a configuration of a treatment planning system for preparing the treatment plan.

First, an operator uses an input device 301 to input information for identifying the patient 106 to be treated by the treatment planning system 300 (for example, name or number allocated to the patient 106 in advance: also called patient identification information). In the treatment planning system 300, the input patient identification information is input to a determination unit 302. The determination unit 302 outputs the patient identification information to an image data fetching unit 303. The image data fetching unit 303 fetches image data of the patient 106 identified by the input patient identification information, from an image server 304. The image data is data of a tomographic image obtained by an X-ray CT apparatus (not illustrated) imaging a target volume of the patient 106. The image server 304 stores in advance the image data of a plurality of patients 106 in association with the patient identification information. The image data fetched by the image data fetching unit 303 is stored in a storage unit 305, and is input to a display controller 306. Based on the input image data, the display controller 306 causes an image display device 307 to display the tomographic image of the target volume of the patient 106.

The operator uses the input device 301 to input information such as a target volume region, an irradiation center position, a body contour, an important organ, position recognizing marker, onto the tomographic image displayed on the image display device 307. The input information is input to a target volume region setting unit 308 via the determination unit 302. The target volume region setting unit 308 associates the input information with the image data, and causes the storage unit 305 to store both of these. Next, the operator causes the input device 301 to input a three-dimensional image display command. The input three-dimensional image display command is provided for a three-dimensional data preparation unit 309 via the determination unit 302. The three-dimensional data preparation unit 309 provided with the three-dimensional image display command prepares three-dimensional body data, based on the image data of the tomographic image stored in the storage unit 305, and causes the storage unit 305 to store the three-dimensional body data. The display controller 306 reads the image data and the three-dimensional body data which are stored in the storage unit 305. Based on both data, the display controller 306 causes the image display device 307 to display the tomographic image and a three-dimensional body image.

While referring to the tomographic image and the three-dimensional body image which are displayed on the image display device 307, the operator uses the input device 301 to input the beam irradiation direction for the target volume. According to the present embodiment, the target volume is irradiated with the beam in the plurality of directions. Accordingly, a plurality of irradiation directions are input by adding the irradiation order. The plurality of input irradiation directions are input to an irradiation direction setting unit 310 via the determination unit 302, thereby determining a tilting degree of the irradiation ports 102a to 102c and the treatment table 108 which are used in each of the plurality of input irradiation directions. The determined tilting degree of the irradiation ports 102a to 102c and the treatment table 108 is associated with the plurality of irradiation directions so as to be stored in the storage unit 305. In a case where the irradiation cannot be performed in the irradiation direction set by the operator, the image display device 307 is caused to display that the irradiation cannot be performed. In addition, the irradiation direction input by the operator is displayed using an arrow by causing the image display device 307 to superimpose the arrow on the tomographic image or the three-dimensional body image. Alternatively, in a case where the orientation of the patient 106 is changed by tilting the treatment table 108, the tomographic image or the three-dimensional body image is tilted and displayed. In this manner, the irradiation direction is easily visible to the operator.

Next, the instrument data preparation unit 311 calculates a depth position of the target volume, a thickness of the target volume, a two-dimensional shape of the outer shape of the target volume, and a shape of the bottom portion of the target volume when the target volume is viewed in the irradiation direction stored in the storage unit 305, based on the three-dimensional body data stored in the storage unit 305. Then, based on the calculation result, when necessary, if scanning irradiation is performed, the instrument data preparation unit 311 obtains energy of the beam extracted from the synchrotron 20 and a current value of the scanning magnet. If broad beam irradiation is performed, the instrument data preparation unit 311 further obtains instrument data such as a value of a current flowing to a wobbler magnet, a thickness of a scatterer, a shape of a range modulator, a shape of a patient collimator, and a patient bolus, and causes the storage unit 305 to store the instrument data. The above-described instrument data is obtained for each irradiation direction.

Next, based on the irradiation direction, the instrument data, and the three-dimensional body data which are stored in the storage unit 305, the dose distribution calculation unit 312 calculates dose distribution of the beam for irradiating the patient 106 with the beam, for each irradiation direction. The dose distribution calculation unit 312 outputs the calculation result of the dose distribution to the display controller 306. Based on the input calculation result of the dose distribution, the display controller 306 causes the image display device 307 to display the dose distribution inside the body of the patient 106.

If the displayed dose distribution is satisfactory, the operator approves the dose distribution. For example, if there is a problem in that a large amount of the dose is distributed to an important organ, the operator changes the irradiation direction, and calculates the dose distribution until the operator can obtain satisfactory dose distribution.

The tilting degree of the irradiation ports 102a to 102c, and the treatment table 108, and the instrument data which correspond to the dose distribution approved by the operator are associated with the patient identification information for each corresponding irradiation direction, and are input to the patient data transmission unit 313 from the storage unit 305. The patient data transmission unit 313 transmits the patient identification information, the irradiation direction, the tilting degree of the irradiation ports 102a to 102c and the treatment table 108, and the instrument data which are input, to a patient data storage device 314. The patient identification information, the irradiation direction, the tilting degree of the irradiation ports 102a to 102c and the treatment table 108, and the instrument data are collectively called patient data. The patient data storage device 314 stores the input patient data, and outputs the patient data in accordance with the request of the irradiation control device 400 or the instrument manufacturing device 315.

When necessary, based on the thickness of the scatterer, the shape of the range modulator, the shape of the patient collimator, and the patient bolus within the patient data stored in the patient data storage device 314, the instrument manufacturing device 315 manufactures the scatterer, the range modulator, the patient collimator, and the patient bolus.

Next, a specific control method of the irradiation device 10a when the irradiation is actually performed based on the previously prepared treatment plan will be described herein with reference to FIG. 4. FIG. 4 is a view illustrating a configuration of the irradiation control device 400.

In the irradiation control device 400, the operator first causes the input device 401 to input the patient identification information of the patient 106 to be treated, and selects the irradiation device to be used. The patient identification information and information identifying the selected irradiation device are input to the determination unit 402 (here, it is assumed that the irradiation device 10a is selected). The patient identification information input to the determination unit 402 is input to a patient data fetching unit 403. Based on the input patient identification information, the patient data fetching unit 403 fetches the corresponding patient data from the patient data storage device 314.

Within the patient data fetched by the patient data fetching unit 403, the irradiation direction for performing the first irradiation is input to a display controller 404. The display controller 404 causes a display device 405 to display the irradiation direction. When necessary, the operator installs the scatterer, the range modulator, the patient collimator, and the patient bolus, which are manufactured in accordance with the irradiation direction displayed on the display device 405, in the irradiation nozzle unit 105.

Within the patient data fetched by the patient data fetching unit 403, the irradiation port (here, the irradiation port 102a) corresponding to the irradiation direction for performing the first irradiation is input to an irradiation nozzle position controller 406, a bending magnet selecting unit 407, and a quadrupole magnet selecting unit 408.

Based on the input irradiation port, the irradiation nozzle position controller 406 controls a drive device 417, and moves the irradiation nozzle unit 105 to a position through which the beam output from the irradiation port 102a passes.

Information for identifying the irradiation device is also input from the determination unit 402 to the bending magnet selecting unit 407. The bending magnet selecting unit 407 selects the bending magnet (in this case, the bending magnets 103a, 103b, and 103d) which has to be excited when the irradiation port 102a is used in the bending magnets configuring the irradiation device 10a, and outputs the information for identifying the selected bending magnet to the magnet power supply controller 409. Energy of the beam extracted from the synchrotron 20 within the patient data is also input to the magnet power supply controller 409. In addition, the information for identifying the irradiation device is also input from the determination unit 402 to the quadrupole magnet selecting unit 408. The quadrupole magnet selecting unit 408 selects the quadrupole magnet (in this case, the quadrupole magnets 104a to 104f) which has to be excited when the irradiation port 102a is used in the quadrupole magnets configuring the irradiation device 10a, and outputs the information for identifying the selected quadrupole magnet to the magnet power supply controller 409.

Based on information for identifying the bending magnet and the quadrupole magnet and the energy which are input, the magnet power supply controller 409 controls an magnet power supply 410, supplies power to the bending magnet and the quadrupole magnet which are identified, and excites the bending magnet and the quadrupole magnet. A value of the power required for the bending magnet and the quadrupole magnet is stored in advance in the magnet power supply controller 409 by being associated with the energy of the beam for each irradiation port. The magnet power supply controller 409 controls each magnet power supply 410 in accordance with the stored power value. Here, as the power value, zero is set for the magnet which does not need to be excited, or the power value is set so as to stop the magnet power supply 410.

Within the patient data fetched by the patient data fetching unit 403, a value of a current provided for an irradiation system magnet is input to an irradiation system magnet power supply controller 411, and the tilting degree of the treatment table is input to a treatment table controller 412. The irradiation system magnet is a scanning magnet 109a as illustrated in FIG. 2 in a case where scanning irradiation is performed, and is a wobbler magnet in a case where wobbler irradiation is performed. In addition, within the patient data fetched by the patient data fetching unit 403, the energy of the beam extracted from the synchrotron 20 is input to a beam energy setting unit 413.

The irradiation system magnet power supply controller 411 controls an irradiation system magnet power supply 414 so as to output the input current value. On the other hand, the treatment table controller 412 controls a treatment table drive device 415 so that the treatment table 108 has the input tilting degree. Furthermore, the beam energy setting unit 413 outputs the input beam energy to an accelerator control device 416. The accelerator control device 416 controls the synchrotron 20 so as to extract the beam having the provided beam energy. A configuration may be adopted in which the tilting degree of the treatment table 108 can be changed by the instruction of the operator through the input device 401.

According to the above-described configuration, preparation for beam irradiation from the irradiation port 102a of the irradiation device 10a is performed.

Then, if the operator uses the input device 401 to input a treatment start command in the preparation is completed, the determination unit 402 receiving the command outputs an extraction start command to the accelerator control device 416. The accelerator control device 416 receiving the extraction start command causes the synchrotron 20 to extract the beam. The beam extracted from the synchrotron 20 is guided to the irradiation device 10a from the irradiation port 102a, and the patient 106 is irradiated with the beam. A dose of the beam used in irradiating the target volume is measured by a dosimeter disposed in the irradiation nozzle unit 105. If the measured value reaches a predetermined setting value, the beam extraction from the synchrotron 20, and the irradiating the target volume with the beam is stopped.

If the beam irradiation is completed in the irradiation direction for the first irradiation as described above, the beam irradiation is performed in the irradiation direction for the second irradiation. The procedure is the same as that in a case of the first irradiation direction, and thus, description thereof will be omitted. However, in a case where the irradiation ports 102a, 102b, and 102c are changed when the irradiation direction is changed, the position of the irradiation nozzle unit 105, the tilting degree of the treatment table 108, and the bending magnet and the quadrupole magnet which are to be excited are changed. When necessary, the scatterer, the range modulator, the patient collimator, and the patient bolus, which are to be installed in the irradiation nozzle unit 105 are also replaced.

In this way, the beam irradiation is repeatedly performed until the irradiation is completely performed in each preset irradiation direction, and the target volume of the patient 106 is irradiated with the beam in the plurality of directions.

Next, a specific structure, a moving mechanism of the irradiation nozzle unit 105, and a specific structure of the cover structure 107 will be described with reference to an overhead view of the irradiation nozzle unit 105 in FIG. 5. FIG. 5 is a view illustrating a schematic configuration when the irradiation nozzle unit 105 and the cover structure 107 are viewed in the direction parallel to the beam irradiation. FIG. 6 is a view illustrating a schematic configuration when the irradiation nozzle unit 105 and the cover structure 107 are viewed from the treatment table 108 side.

As illustrated in FIG. 5, the scanning magnets 109a, 109b, and 109c, and the wobbler magnet are disposed on the vacuum ducts 102a, 102b, and 102c side, and are installed on a beam upstream side from the cover structure 107.

A monitor 510 and a compensator 501 are installed inside the irradiation nozzle unit 105. For example, as the monitor 510, a dose monitor or a beam position monitor for measuring the flatness of the beam are installed. In addition, for example, as the compensator 501, a range modulator (range adjuster) for adjusting a beam reaching depth by adjusting the energy of the beam, a scatterer, a ridge filter patient collimator, a patient bolus, and an applicator are installed.

In addition, the cover structure 107 is fixed to the floor 101 or the side wall 113 of the treatment room so as to separate the space having the irradiation nozzle unit 105 installed therein and the space having the plurality of irradiation ports 102a, 102b, 102c installed therein from each other. As illustrated in FIGS. 5 and 6, the cover structure 107 has a first support member 503A and a second support member 503B which support the irradiation nozzle unit 105 from both sides, and two slits 110 for allowing the first support member 503A and the second support member 503B to move through the rear side of the cover structure. The cover structure 107 between the two slits 110 is formed from one or more plates, and upper and lower ends thereof are fixed to two cover support members 112 fixed to the floor 101 and the side wall 113 of the treatment room so that both sides of the cover structure 107 are interposed between the cover support members 112. In the cover support member 112, the cover structure 107 is replaceable by detaching and changing the cover structure 107 from the cover support member 112.

In addition, as illustrated in FIG. 5, the moving mechanism for enabling the irradiation nozzle unit 105 to move between the plurality of irradiation ports 102a, 102b, and 102c is disposed on the space where the plurality of irradiation ports 102a, 102b, and 102c of the cover structure 107 are installed.

The moving mechanism for moving the irradiation nozzle unit 105 has a drive device 417 formed from a drive motor, a gear 506 which is rotated by the rotation of the drive device 417, and a guide rack 504A and a guide rail 504B which mesh with the gear 506 and which guide the movement of the irradiation nozzle unit 105 between the plurality of irradiation ports 102a, 102b, and 102c. The guide rack 504A and the guide rail 504B are arranged so as to interpose the irradiation ports 102a, 102b, and 102c therebetween when viewed in the direction vertical to the moving direction of the irradiation nozzle unit 105. The guide rack 504A and the guide rail 504B are arranged to be parallel to the cover structure 107 when viewed in the direction parallel to the moving direction of the irradiation nozzle unit 105.

The irradiation nozzle unit 105 is supported for the moving mechanism by the first support member 503A and the second support member 503B which are disposed in both side end portions. More specifically, the end portion of the first support member 503A is supported by the guide rack 504A via the gear 506, and the end portion of the second support member 503B is supported by the guide rail 504B.

When the irradiation nozzle unit 105 is moved between the plurality of irradiation ports 102a, 102b, and 102c, the drive device 417 is driven. The gear 506 is rotated by the drive device 417 being driven. The tooth of the gear 506 meshes with the tooth disposed in the guide rack 504A. Accordingly, the irradiation nozzle unit 105 moves to a position corresponding to the predetermined irradiation ports 102a, 102b, and 102c in the rotation direction of the gear 506 along the guide rack 504A.

Next, an advantageous effect according to the present embodiment will be described.

In the above-described particle beam treatment system according to Embodiment 1 of the present invention, the irradiation devices 10a and 10b have the plurality of irradiation ports 102a, 102b, and 102c for respectively irradiating the target with the particle beam in the plurality of directions. In addition, the irradiation nozzle unit 105 of the irradiation devices 10a and 10b is movable between the plurality of irradiation ports 102a, 102b, and 102c. The fixed cover structure 107 is disposed between the plurality of irradiation ports 102a, 102b, and 102c and the irradiation nozzle unit 105. In addition, the cover structure 107 has the slit 110 for allowing the support member (first support member 503A and second support member 503B) supporting the irradiation nozzle unit 105 to pass therethrough. Furthermore, the irradiation nozzle unit 105 is formed to be movable separately from the irradiation ports 102a, 102b, and 102c, and has the structure in which the vacuum duct is not disposed inside the irradiation nozzle unit 105.

In a case where the distal end of the irradiation nozzle unit 105 is movable in the circumferential direction while being oriented to the irradiation target, the fixed cover structure 107 is used in order to form an access floor or to function as a cover for concealing the drive structure for moving the irradiation nozzle. Therefore, it is no longer necessary to install a moving floor which is deformable along the movement of the irradiation nozzle, and it is no longer necessary to provide a complicated mechanism. In addition, the number of drive systems can be considerably reduced. Accordingly, the frequency of carrying out maintenance work can be considerably reduced compared to the related art, and it is possible to provide the particle beam treatment system which is very excellent in maintainability. Furthermore, the irradiation nozzle unit 105 is shared in use with the plurality of irradiation ports 102a to 102c. Accordingly, compared to a case where the irradiation nozzle is disposed for each of the plurality of irradiation ports, the number of irradiation nozzles can be minimized. Therefore, there is an advantageous effect in that the cost of the irradiation device can be reduced.

In addition, in a case of a system in which the particle beam for irradiation is formed of helium, argon, and carbon whose mass is heavier than that of the proton, particularly in a case of a system in which the particle beam is formed of a heavy particle, a longer distance is required in order to change the position of the beam. Thus, the scanning magnets 109a, 109b, and 109c and the wobbler magnet are arranged to be separate to the upstream side from the outlet of the irradiation nozzle in the last linear portion of the irradiation device. Therefore, in a case where the present invention is applied to the system using the ion whose mass is heavier than that of the proton, a space suitable for installing the cover structure is easily secured between the monitor or the compensator and the scanning magnet. Accordingly, the cover structure can employ a simplified structure for which maintenance work is more easily carried out.

In addition, in the case where the present invention is applied to the system using the ion whose mass is heavier than that of the proton, the heavy mass ion relatively less scatters in the air. Therefore, even in a case where the nozzle irradiation unit and the irradiation port are structurally separated from each other in order to install the cover structure, and the end portion of the vacuum duct is extended to the cover structure, the irradiation accuracy can be more easily maintained.

Furthermore, it is preferable that the nozzle unit having the monitor and the compensator mounted thereon is assembled to the cover structure. It is more preferable that a thin irradiation nozzle unit having only the monitor mounted thereon is assembled to the cover structure. In this manner, the irradiation accuracy can be more easily maintained.

Furthermore, the moving mechanism for moving the irradiation nozzle unit 105 has the drive device 417, the gear 506 which is rotated by the rotation of the drive device 417, and the guide rack 504A which meshes with the gear 506 and which guides the movement of the irradiation nozzle unit 105 between the plurality of irradiation ports 102a, 102b, and 102c. In this manner, the irradiation nozzle unit 105 can very accurately move using the simple structure between the irradiation ports 102a, 102b, and 102c, and can be aligned with the irradiation ports 102a, 102b, and 102c. Accordingly, it is possible to provide the particle beam treatment system which can very accurately perform the irradiation while the simple structure is used.

In addition, the moving mechanism further has the guide rail 504B which guides the movement of the irradiation nozzle unit 105 between the plurality of irradiation ports 102a, 102b, and 102c. In this manner, the irradiation nozzle unit 105 can more stably move between the irradiation ports 102a, 102b, and 102c, and can be aligned with the irradiation ports 102a, 102b, and 102c.

Furthermore, the guide rack 504A and the guide rail 504B are arranged so as to interpose the irradiation port 102a, 102b, and 102c therebetween. The cover structure 107 has the two slits 110, and the irradiation nozzle unit 105 is supported in the moving mechanism by the first support member 503A located on the guide rack 504A side and the second support member 503B located on the guide rail 504B side. In this manner, the irradiation nozzle unit 105 is supported for the moving mechanism by the two support members. Accordingly, the irradiation nozzle unit 105 can more stably move between the irradiation ports 102a, 102b, and 102c, and can be aligned with the irradiation ports 102a, 102b, and 102c.

In addition, the cover structure 107 between the two slits 110 is formed from one or more plates, and is formed so as to be replaceable by detaching and changing the cover structure 107 from the cover support member 112. In this manner, even if the cover structure 107 is consumed due to the irradiation, the cover structure 107 can be easily replaced. Accordingly, it is possible to provide the particle beam treatment system which is excellent in maintainability while the structure is further simplified.

<Embodiment 2>

Embodiment 2 of the particle beam treatment system according to the present invention will be described with reference to FIG. 7. FIG. 7 is a view illustrating a schematic configuration when the irradiation nozzle and the cover member according to the present embodiment are viewed from the treatment table side.

As illustrated in FIG. 7, a cover structure 107A disposed in the particle beam treatment system according to the present embodiment has a hole 111 disposed at a position corresponding to the plurality of irradiation ports 102a, 102b, and 102c.

Other configurations and operations are substantially the same as the configurations and the operations of the particle beam treatment system according to Embodiment 1 described above, and thus description thereof will be omitted.

The particle beam treatment system according to Embodiment 2 of the present invention can also obtain substantially the same advantageous effect as that of the particle beam treatment system according to Embodiment 1 described above.

In addition, the cover structure 107A has the hole 111 disposed at the position corresponding to the plurality of irradiation port 102a, 102b, and 102c. In this manner, it is possible to further reduce substances which cause the particle beam to scatter during the irradiation. Accordingly, the more accurate irradiation can be performed. In addition, it is possible to further reduce the consumption of the cover structure 107A which is caused by the irradiation, thereby providing the particle beam treatment system which is more excellent in maintainability.

The hole 111 of the cover structure 107A can employ a structure like a window by disposing a member having high radiation permeability.

<Embodiment 3>

Embodiment 3 of the particle beam treatment system according to the present invention will be described with reference to FIG. 8. FIG. 8 is a view illustrating a schematic configuration when the irradiation nozzle and the cover member according to the present embodiment are viewed in the direction parallel to the beam irradiation.

As illustrated in FIG. 8, similarly to Embodiment 2, the cover structure 107A disposed in the particle beam treatment system according to the present embodiment has the hole 111 disposed at the position corresponding to the plurality of irradiation ports 102a, 102b, and 102c.

In addition, according to the present embodiment, the cover 114 is disposed on a side closest to the hole 111 of the cover structure 107A of the plurality of irradiation ports 102a, 102b, and 102c, that is, on the utmost downstream side of the vacuum ducts 102a, 102b, and 102c located at the position closest to the target.

Other configurations and operations are substantially the same as the configurations and the operations of the particle beam treatment system according to Embodiment 1 described above, and thus description thereof will be omitted.

The particle beam treatment system according to Embodiment 3 of the present invention can also obtain substantially the same advantageous effect as that of the particle beam treatment system according to Embodiment 1 described above.

In addition, the plurality of irradiation ports 102a, 102b, and 102c have the cover 114 disposed at the position closest to the target. In this manner, in a case where the irradiation nozzle unit 105 is not present after moving, it is possible to prevent the utmost downstream side of the vacuum duct 102a, 102b, and 102c from being directly exposed to the treatment room. Accordingly, the durability of the vacuum duct 102a, 102b, and 102 can be lengthened. Therefore, it is possible to provide the particle beam treatment system which is more excellent in maintainability.

<Others>

The present invention is not limited to the above-described embodiments, and includes various modification examples. The embodiments have been described in detail in order to facilitate the understanding of the present invention, and are not necessarily limited by those which include all of the described configurations. In addition, configurations according to a certain embodiment can be partially replaced with configurations according to the other embodiment. Alternatively, the configurations according to the other embodiment can be added to the configurations according to a certain embodiment. In addition, the configurations according to each embodiment can partially adopt the other configuration which is added, deleted, or replaced.

For example, as long as the required number of quadrupole magnets can optimize beam parameters in a target volume, the number of quadrupole magnets installed in the irradiation device may be optionally selected without being limited to the number of quadrupole magnets described in the embodiments.

In addition, as long as instead of the scanning magnet or the wobbler magnet, an instrument is disposed in the irradiation nozzle and is automatically controllable, the instrument may be controlled by the irradiation control device 400.

Furthermore, in the above-described embodiment, an example has been described in which two irradiation devices are disposed for the synchrotron 20. However, the number of irradiation devices is not limited to two.

In addition, in the above-described embodiment, an example has been described in which three irradiation ports are provided. However, the number of irradiation ports is not limited to three. As long as a plurality of irradiation ports are provided, the number may be two or four.

Furthermore, an example has been described in which the synchrotron is used as the accelerator of the heavy particle beam. However, other accelerators such as a cyclotron accelerator and a linear accelerator may be used.

In addition, the heavy particle beam irradiation system for irradiating the irradiation target with the heavy particle ion such as carbon has been described as an example. However, the particle beam used in irradiating the irradiation target is not limited to the heavy particle ion. The present invention is also applicable to the proton whose mass is lighter than that of the heavy particle, a particle whose mass is heavier than that of the proton except for the carbon, or a neutron.

REFERENCE SIGNS LIST 10a, 10b: IRRADIATION DEVICE
20: SYNCHROTRON
30a, 30b: SWITCHING MAGNET
40a, 40b: POWER SUPPLY
50: BEAM DUMP
101: FLOOR
102a, 102b, 102c: IRRADIATION PORT (VACUUM DUCT)
103a, 103b, 103c, 103d: BENDING MAGNET
104a, 104b, 104c, 104d, 104e, 104f, 104g, 104h, 104i, 104j: QUADRUPOLE MAGNET
105: IRRADIATION NOZZLE UNIT (IRRADIATION NOZZLE)
107, 107A: COVER STRUCTURE (THE COVER MEMBER)
108: TREATMENT TABLE
109a, 109b, 109c: SCANNING MAGNET
110: SLIT
111: HOLE
112: COVER SUPPORT MEMBER
113: SIDE WALL
114: COVER
300: TREATMENT PLANNING SYSTEM
301: INPUT DEVICE

302: DETERMINATION UNIT
303: IMAGE DATA FETCHING UNIT
304: IMAGE SERVER
305: STORAGE UNIT
306: DISPLAY CONTROLLER
307: IMAGE DISPLAY DEVICE
308: TARGET VOLUME REGION SETTING UNIT
309: DIMENSION DATA PREPARATION UNIT
310: IRRADIATION DIRECTION SETTING UNIT
311: INSTRUMENT DATA PREPARATION UNIT
312: DOSE DISTRIBUTION CALCULATION UNIT
313: PATIENT DATA TRANSMISSION UNIT
314: PATIENT DATA STORAGE DEVICE
315: INSTRUMENT MANUFACTURING DEVICE
400: IRRADIATION CONTROL DEVICE
401: INPUT DEVICE
402: DETERMINATION UNIT
403: PATIENT DATA FETCHING UNIT
404: DISPLAY CONTROLLER
405: DISPLAY DEVICE
406: IRRADIATION NOZZLE POSITION CONTROLLER
407: BENDING MAGNET SELECTING UNIT
408: QUADRUPOLE MAGNET SELECTING UNIT
409: MAGNET POWER SUPPLY CONTROLLER
410: MAGNET POWER SUPPLY
411: IRRADIATION SYSTEM MAGNET POWER SUPPLY CONTROLLER
412: TREATMENT TABLE CONTROLLER
413: BEAM ENERGY SETTING UNIT
414: IRRADIATION SYSTEM MAGNET POWER SUPPLY
415: TREATMENT TABLE DRIVE DEVICE
416: ACCELERATOR CONTROL DEVICE
417: DRIVE DEVICE (DRIVE MOTOR)
501: COMPENSATOR
503A: FIRST SUPPORT MEMBER
503B: SECOND SUPPORT MEMBER
504A: GUIDE RACK
504B: GUIDE RAIL
506: GEAR
510: MONITOR

The invention claimed is:

1. A particle beam treatment system comprising:
an accelerator that accelerates a particle beam;
a beam transport system that transports the particle beam accelerated by the accelerator;
an irradiation device that has an irradiation nozzle for irradiating a target with the particle beam transported by the beam transport system; and
a controller configured to control the accelerator, the beam transport system, and the irradiation device,
wherein the irradiation device has a plurality of irradiation ports for irradiating the target with the particle beam in a plurality of directions,
wherein the irradiation nozzle of the irradiation device is movable between the plurality of irradiation ports, and
wherein a fixed cover member is disposed between the plurality of irradiation ports and the irradiation nozzle.

2. The particle beam treatment system according to claim 1,
wherein the particle beam includes a particle whose mass is heavier than the mass of a proton.

3. The particle beam treatment system according to claim 1,
wherein a moving mechanism that moves the irradiation nozzle has a drive motor, a gear which is rotated by the rotation of the drive motor, and a guide rack which meshes with the gear so as to guide the irradiation nozzle to move between the plurality of irradiation ports.

4. The particle beam treatment system according to claim 3,
wherein the moving mechanism further has a guide rail which guides the irradiation nozzle to move between the plurality of irradiation ports.

5. The particle beam treatment system according to claim 4,
wherein the guide rack and the guide rail are disposed so as to interpose the irradiation port therebetween, and
wherein the irradiation nozzle is supported in the moving mechanism by a first support member located on the guide rack side and a second support member located on the guide rail side.

6. The particle beam treatment system according to claim 1,
wherein the cover member has holes respectively corresponding to positions of the plurality of irradiation ports.

7. The particle beam treatment system according to claim 1,
wherein the cover member is replaceable.

8. A particle beam treatment system comprising:
an accelerator that accelerates a particle beam;
a beam transport system that transports the particle beam accelerated by the accelerator; and
an irradiation device that has an irradiation nozzle for irradiating a target with the particle beam transported by the beam transport system,
wherein the irradiation device has a plurality of irradiation ports for irradiating the target with the particle beam in a plurality of directions,
wherein a fixed cover member is disposed between the plurality of irradiation ports and the irradiation nozzle, and
wherein the cover member has at least one slit for allowing a support member for supporting the irradiation nozzle to pass therethrough.

9. The particle beam treatment system according to claim 8,
wherein the cover member has two slits formed at two locations in the cover member.

10. The particle beam treatment system according to claim 9,
wherein the cover member between the two slits includes one or more plates, and is formed so as to be replaceable.

* * * * *